(12) United States Patent
Von Arx

(10) Patent No.: US 8,839,795 B2
(45) Date of Patent: Sep. 23, 2014

(54) FACE AND MOUTH MUSCLE STIMULATOR

(76) Inventor: Jose Duran Von Arx, Barcelona (ES)

( * ) Notice: Subject to any disclaimer, the term of this patent is extended or adjusted under 35 U.S.C. 154(b) by 361 days.

(21) Appl. No.: 12/733,662

(22) PCT Filed: Sep. 10, 2008

(86) PCT No.: PCT/ES2008/000582
§ 371 (c)(1),
(2), (4) Date: Mar. 12, 2010

(87) PCT Pub. No.: WO2009/034205
PCT Pub. Date: Mar. 19, 2009

(65) Prior Publication Data
US 2010/0211150 A1    Aug. 19, 2010

(30) Foreign Application Priority Data

Sep. 14, 2007 (ES) .................................. 200702446
Jun. 30, 2008 (ES) .................................. 200801949
Jul. 1, 2008 (ES) .................................. 200801972

(51) Int. Cl.
*A61C 5/14* (2006.01)
*A61F 11/00* (2006.01)
*A63B 23/03* (2006.01)
*A61C 7/36* (2006.01)

(52) U.S. Cl.
CPC *A63B 23/032* (2013.01); *A61C 7/36* (2013.01)
USPC .......................................... 128/859; 128/857

(58) Field of Classification Search
USPC ......... 128/859, 857, 861, 846, 848, 862, 860;
602/902, 41; 433/6, 140, 229, 93;
600/237, 238; 601/139, 138, 136;
606/204.15, 235, 234; 607/134
See application file for complete search history.

(56) References Cited

U.S. PATENT DOCUMENTS

| 506,457 | A | * | 10/1893 | Waite ............................... 56/257 |
| 1,483,694 | A | | 2/1924 | Stukey et al. |
| 2,178,128 | A | * | 10/1939 | Waite ............................ 128/848 |
| 5,682,903 | A | | 11/1997 | Meade et al. |
| 6,302,110 | B1 | | 10/2001 | Yoshida et al. |
| 6,427,696 | B1 | | 8/2002 | Stockhausen |
| 6,676,616 | B1 | * | 1/2004 | Hagiwara ..................... 601/139 |

FOREIGN PATENT DOCUMENTS

| ES | 2151837 | 1/2001 |
| GB | 506457 | 5/1939 |

(Continued)

OTHER PUBLICATIONS

2006, HowStuffWorks, <http://static.ddmcdn.com/gif/kissing-9.jpg>.*

(Continued)

*Primary Examiner* — Victoria J Hicks

(57) ABSTRACT

The invention relates to a face and mouth muscle stimulator formed by an approximately oblong, oval body (1) to be placed in the mouth, having an open central part and side ends (2) that are wider than the upper and lower mid-zones (3) which are provided with V-shaped recesses (4) at the position of the frenulum. Optionally, the invention can include fixed or removable projections (5) positioned on the stimulator or on attachments (8). The invention can also include a sheet (6) provided with holes (7) for the connection of elements such as bottles or pacifiers or provided with a horizontal groove (11) for the incorporation of a bite splint (12) coupled at the front (2*b*) thereof using T-shaped flanges (13). Alternatively, the body (1') can have a V-shaped configuration formed by vertical walls (20 and 30) in order to be positioned in the inner space of the lower jaw, including perpendicular projections (40 and 50) by way of horizontal bite planes.

1 Claim, 5 Drawing Sheets

(56) References Cited

FOREIGN PATENT DOCUMENTS

| | | |
|---|---|---|
| GB | 2353709 | 3/2001 |
| WO | 94/23674 | 10/1994 |

OTHER PUBLICATIONS

International Search Report mailed Jan. 1, 2009, International Application No. PCT/ES2008/000582, 4 pages.

\* cited by examiner

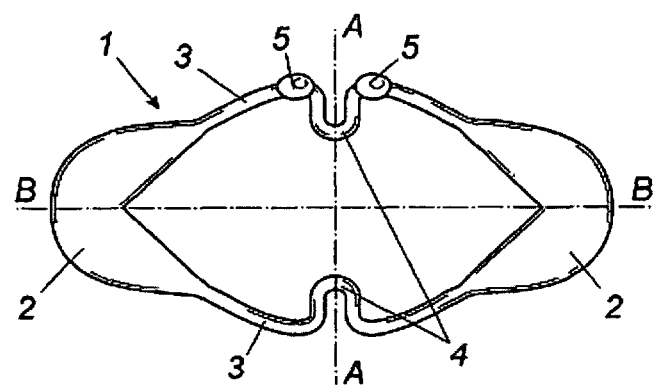
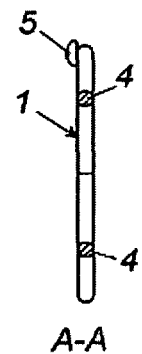
Fig. 1  Fig. 2
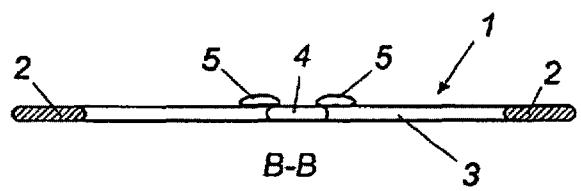
Fig. 3
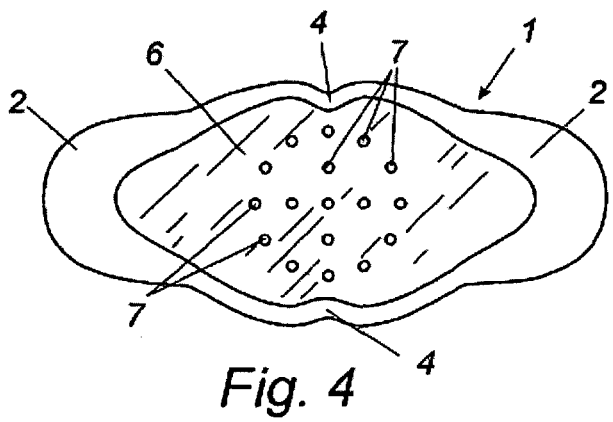
Fig. 4

FACE AND MOUTH MUSCLE STIMULATOR

PURPOSE OF THE INVENTION

As expressed in the title of this design brief, the invention refers to a face and mouth muscle stimulator.

More specifically, the object of the invention consists in a prefabricated physical element made of biocompatible and elastic materials and used inside the mouth, which is especially developed and designed to apply stimulation to the face muscles, offering medium or long-term effects that modify muscle tone, muscle functions and/or the expression of the user's face.

The stimulator has been designed for use inside the mouth, between the teeth and the lips or the cheeks, and it will be principally used at night, although it can also be used during the day.

As is well known, the application of direct stimulation to certain muscles or muscle groups stimulates them and inhibits the activity of the antagonist muscles.

This stimulator bases its action on the aforementioned physiological principle. In order to do this, stimulant elements can be added or removed to the basic shape, which will act on different points of the mouth cavity, according to their location on the body of the stimulator, being either built into the design or added or removed by means of insertion systems incorporated to the basic shape.

To introduce these muscle-stimulating effects at a very early age, the invention includes the adaptation of the stimulator to elements commonly used for small children, such as baby's bottles or dummies. For young people or adults, the stimulator will come in different sizes as well as different hardnesses.

In addition, the invention contemplates the incorporation, to a specific purpose-designed variant of the stimulator, of an additional biting element, known as a bite splint, especially designed to reduce bruxism problems, so that, at the same time as certain face muscles are stimulated and the activity of the antagonist muscles is inhibited, it is an effective tool against the problems caused by gnashing teeth.

Finally, there is another variant of the stimulator designed as a mouth stimulation element for the muscles of mastication, with the aim of exercising lax chewing muscles.

For this purpose, the stimulating element is designed to be placed inside the mouth, between the upper and lower jaws, with a design that can the user can bite, as well as with a design that prevents the pressure of the tongue on the front teeth. Its will also be used mainly at night, although it can be used during the day.

APPLICATION OF THE INVENTION

The area of application of this invention is in dentistry (especially in the field of orthodontics), miofunctional re-education, physiotherapy, otolaryngology, facial aesthetics & other medical fields.

BACKGROUND OF THE INVENTION

Stimulation of muscles is used in certain removable orthodontic apparatus, but they cannot be used in treatments with fixed apparatus, therefore work based on the use of prefabricated apparatus that can be combined with the use of fixed orthodontic apparatus would be very beneficial for muscular and functional re-education in orthodontics.

In addition, the possibility of applying these principles at early ages introduces a new scope of action for prefabricated elements, favouring early muscular re-education. In adult subjects, the possibility of remodelling the facial expression and balancing facial aesthetics is a novel field of application for item.

It is also known that bruxism is a very common dental pathology, negatively affecting the positioning of teeth, which because of excess continuous pressure exerted involuntarily by the patient, are affected by premature wear as well as unadjusted occlusions.

The most common and effective treatment against this dysfunction, consists in placing dental protection, known as a bite splint, which consists of a body of suitable material, generally resin or plastic, placed in the mouth between the teeth so that when the jaws are closed, pressure is exerted on it, i.e., it is bitten.

In addition, the bite splint, from the first days of its use, eliminates jaw, head or ear pain, as well as other discomfort arising due to strain on the jaw muscles and even without the use of the ferrule, may cause dizziness because of the great pressure exerted on the jaw.

However, the ferrule conventionally consists simply of a body placed between the teeth, with no more securing than that exerted by the patient, being made from plaster moulds of the patient, thus needing the intervention of a prosthetic laboratory. Current ferrules have no beneficial effects other than the discharge of pressure on them.

Therefore, another objective of this invention is the incorporation of a frontal bite splint or biting plane, taking advantage of the structural features of the stimulating element for securing it, as well for exerting, simultaneously, the described stimulation of certain facial muscles, which will alleviate problems caused by bruxism.

Finally, it is also know that mastication activity is the effect of neuromuscular operation on two main levels: The mastication muscles: Temporal, Masseter, Pterigoids, (internal and external) in combination with coordinated tongue movement. The operation of these muscles is fundamental for chewing and consequently for digestion, as chewing is the first step in good digestion, and therefore any alterations or illnesses of these muscles will require special attention.

Therefore, to promote their exercise in patients who, for whatever reason, suffer from problems of this kind, it is necessary to create instruments to help this work, stimulating the muscles of mastication so they are exercised, thus increasing their strength and mobility, another of the objectives of the this invention, highlighting the fact that, currently, and by reference to the state of the art, by the petitioner, no face and mouth muscle stimulators present technical, structural and features similar to this invention are known to exist, the invention aiming to contribute to the field of the orthodontics and miofuntional re-education, orthodontic prevention and facial aesthetics the aforementioned benefits and alleviate the effects of the aforementioned dysfunctions.

EXPLANATION OF THE INVENTION

The face and mouth muscle stimulator proposed in this invention, is an evident novelty in its field, as due to its application mentioned above, specific stimulation of certain facial muscles or groups of muscles is specifically achieved to obtain for stimulation of them (direct action) or inhibition of the antagonist muscle activity (indirect action), carrying out a "remodelling" of the facial expression and/or of its muscular functions. Another aspect achieved is a way to secure a bite splint, while at the same time stimulating certain facial muscles with a favourable effect on the alleviation of bruxism, as well stimulating the muscles of mastication to provoke their exercise, the details being characterised that make all this possible, properly described in the final claims that accompany this invention.

For this purpose, the face muscle stimulator of the invention consists, essentially, in a prefabricated physical element, made of biocompatible and elastic materials, destined to be placed inside the mouth, between the teeth and the lips or cheeks, which is basically made up of an essentially flat body that will adopt an approximately oval shape, with wider edges than the middle lower and upper areas, in the centre of which, there are some V-shaped scallops corresponding to the inlays of the frenulum of the lower and upper lips respectively.

This basic shape is totally open or hollow in its centre, enabling the free circulation of air, although it can be optionally closed with a strip, which when it obliterates or impedes this passage, it will have holes (larger or smaller) to regulate the passage of air.

It is also important to highlight that the basic shape of the stimulator, in addition to having possible slight variations as regards thickness, edge and side shape, can also incorporate built-in stimulation points in different areas, consisting of pairs of small projections that can be attached to the body in a permanent or removable manner by means of conventional attachment systems, which, according to their position, will act on different muscles or groups of muscles:

The basic open body without specific stimulation points; stimulates the upper and lower orbicularis muscles directly, increasing the tone of the lips. Indirectly (effect on the antagonist muscles) it achieves the effect of positioning the tongue at the rear.

The open body with specific front and upper stimulation points stimulates the upper orbicularis muscle and favours the lengthening of the upper lip.

The open body with specific front and lower stimulation points acts on the labiomental muscles and relaxes them when they are contracted.

The open body with specific front and upper side stimulation; stimulates the side muscles that lift the upper lip and the corner of the mouth.

The open body with specific front and lower side stimulation; stimulates the side muscles that depress the lower lip and the corner of the mouth.

The open body with specific rear and upper side stimulation; stimulates the risorius muscle and favours the action of smiling.

The open body with specific side rear and lower stimulation; stimulates the cheek depressor muscles, favouring a more serious facial expression.

The open body, depending on the design of its side ends, stimulates the back (upper and lower) of the side vestibules of the mouth, creating tension at the point of the muscular inserts of the area, causing (indirectly) the inhibition of the tone of the muscles of mastication. This effect is positive for individuals suffering from bruxism or "clamped teeth". This side stimulation is wider (more extensive) than the aforementioned and more intense. It requires a modification of the side ends of the basic body, consisting in these ends being slightly lengthened so they cover the depth of the mouth vestibule.

It can be highlighted that, to facilitate its use in very early ages, the body described may also be attached to other commonly used elements such as baby bottles, dummies or others, the effects being the same as those of the open body without specific stimulation, i.e., stimulating directly the upper and lower orbicularis muscles and increasing the tone of the lips. Indirectly (effect on the antagonist muscles) it achieves the effect of positioning the tongue at the rear. This second effect (Indirect) will favour the giving up of the dummy sucking habit.

There is an alternative variant of the stimulator, especially designed to alleviate bruxism, which has a horizontal groove in its central area that can receive an additional part conforming a bite splint, which consists of a body, made of suitable material such as resin or plastic.

This body, making up the ferrule, consists essentially of two parts, a flat rear part and with an approximately circular shaped plan section, so it can be placed between the teeth of the upper and lower jaws, to be bitten, and another frontal, perpendicular to the former, which has an approximately rectangular shape, joined by its centre to the edge of the rear part, and from which emerge T-shaped flaps from the front that can be inserted in the mentioned horizontal groove designed for this purpose in the body of the stimulator.

We can highlight that the described body forming the ferrule can be of different sizes to adapt to the dimensions of the user's mouth in each case, as they will not be the same, for instance, in an adult person or a small child.

Finally, another variant of the stimulator will adopt a structural configuration that essentially comprises an approximately V-shaped plan, the arms of which are vertical walls of a regular thickness, that will be placed in the inner space of the lower jaw, with, in the upper parts of the arms, projections that are perpendicular towards the outside, apt and destined to be biting planes, i.e., apt for placement between the molars of both lower and upper jaw, to be bitten.

The vertex of the mentioned V, conforming the body of the part, is slightly raised, extended in its centre to determine a central appendix that is slightly curved, forming a sort of frontal shield, apt and destined to support the tongue, with the internal part of this vertex bearing a series of rough spots designed to stimulate the position of the tongue making it tend to be placed on them.

Therefore, the lateral biting planes stimulate the muscles of mastication with the intention exercising them, principally for patients with lax chewing muscles.

The frontal shield impedes the pressure of the tongue on the front teeth, which would cause an undesired effect on the teeth, and the rough spots on the inner part act as stimulation to "deceive" the tongue, and make it rest on them.

The new face and mouth muscle stimulator is therefore an innovative structure with novel structural and constructive features, reasons that, as well as its practical usefulness, are sufficient rationale for granting it the requested exclusivity.

DESCRIPTION OF THE DRAWINGS

In order to complement this description and in order to facilitate a better understanding of the features of the invention, a set of drawings forming an integral part of the invention are attached to this descriptive report showing the following for illustration but not limiting purposes:

FIG. 1.—Displays a plan view of an example of the new face and mouth muscle stimulator, in which the main parts and elements that conform it, as well their configuration and layout can be observed.

FIGS. 2 and 3.—Displaying vertical and horizontal section views, according to the corresponding planes A-A and B-B indicated in FIG. 1.

FIG. 4.—Displaying a plan view of another example of facial stimulator, in this case incorporating a strip sealing its central area.

PREFERRED EMBODIMENT OF THE INVENTION

Figure 5:
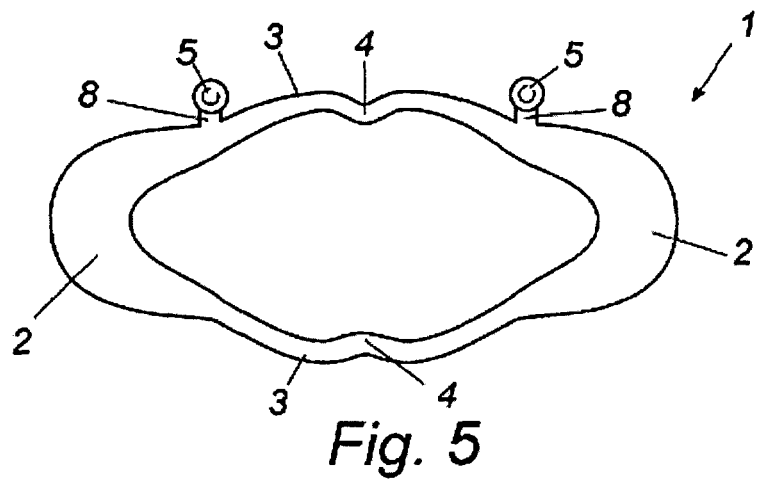
FIG. 5.—Displaying another example of a facial stimulator in which the stimulation points are placed in external projections.

Referring to the aforementioned figures and following their numeration, it can be seen how the face and mouth muscle stimulator described is essentially formed by a body (1) made of biocompatible materials, designed to be placed between a front side of teeth of a patient and an internal side of lips of the patient. The body (1), is essentially flat, with an approximately oval plan, open in its central part, as can be seen in FIGS. 1 to 3, the ends, or opposing side portions, (2) being wider than the upper and lower middle zones (3), in the centre of which are some crenated or V-shaped recesses (4), deeper or shallower, as necessary for each case, corresponding to the insertions of the frenulum of the lower and upper lips respectively.

The aforementioned body (1) may also incorporate specific stimulation points, designed to act on different muscles or groups of muscles, depending on their position, consisting of small projections (5) that may be optionally fitted to the body (1) permanently or removable, by means of conventional fitting systems such as adhesives or similar. More specifically, as depicted in FIG. 1, stimulation points in the form of removable protuberances (5) project outward from a front face of at least one of the opposing upper and lower zones (3), wherein the one or more stimulation points (5) are configured to act on muscle groups in the mouth of a patient.

Thus, these projections can be positioned, preferably in pairs, both on the front and rear areas of the upper and/or lower middle zones (3) of the body (1), achieving different results on the facial muscles according to their position.

As can be seen in the example in FIG. 5, the mentioned projections (5) or stimulation points may also be fitted to the body (1) of the stimulator on outer projections (8) designed for this purpose in the necessary position, thus enlarging the field of action within the mouth cavity.

As described above, this body (1) is totally open in its centre, to enable the free passage of air, although it can optionally be closed with a membrane or strip (6) which, when this obliterates or hinders the passage of air, it will have some holes (7) (larger or smaller) for breathing, as represented in FIG. 4.

Figure 6:
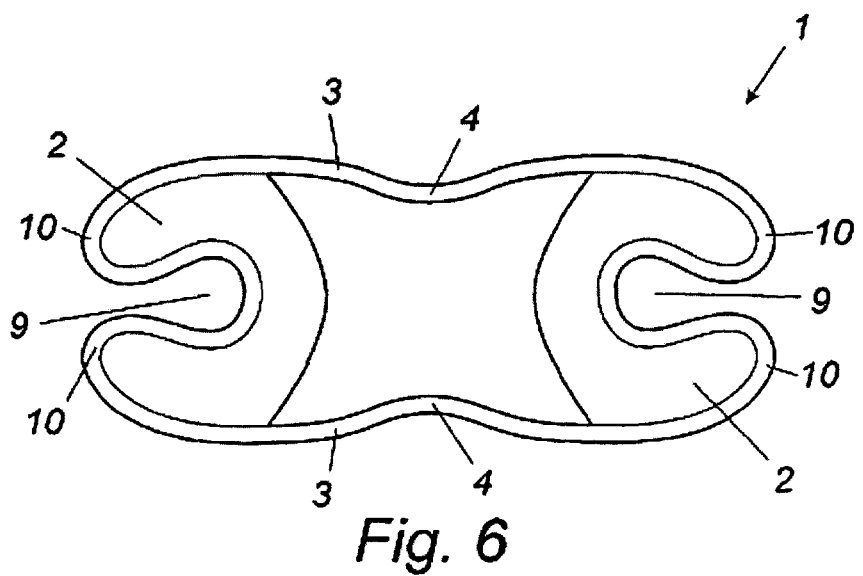
FIG. 6.—Shows another example of stimulator in which the shape of its side ends has been changed to stimulate lateral zones and muscles in the mouth cavity.

As can be seen in FIG. 6, the ends or side zones (2) of the body (1) can have different alternative shapes, as represented in the figure, forming an internal curve (9) that determines two rounded areas (10), which, thanks to the flexibility of the material the stimulator is made of, will provide a massage that stimulates the areas and muscles located in the part of the mouth cavity they come into contact with.

It can also be highlighted that the body (1), which will generally be used alone, is advantageously apt to fit to other elements used in the mouth, such as baby bottles, dummies, etc., thus facilitating use with very young children.

Figure 7:
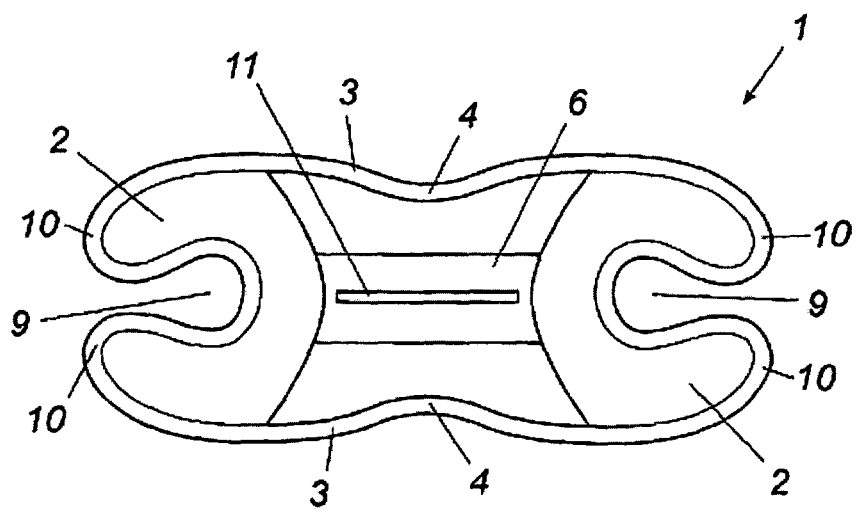
FIG. 7.—Shows a plan view of the example of stimulator displayed in FIG. 6, to which a membrane or central strip has been incorporated, to fit the bite splint.
Figure 8:
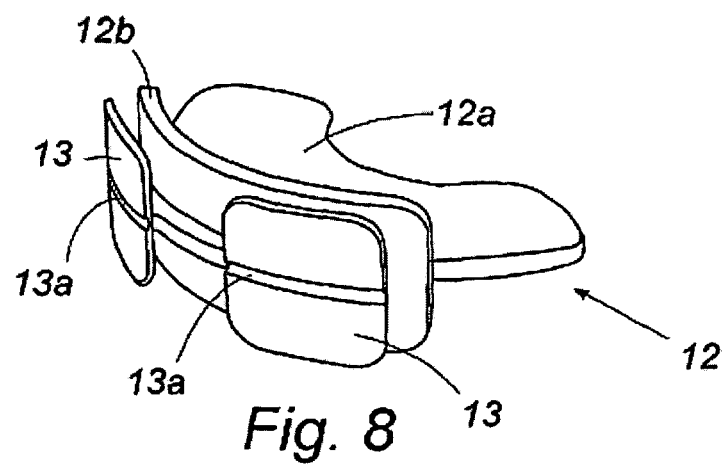
FIG. 8.—Shows a perspective view of the ferrule that can be fitted to the stimulator, according to the invention.
Figure 9:
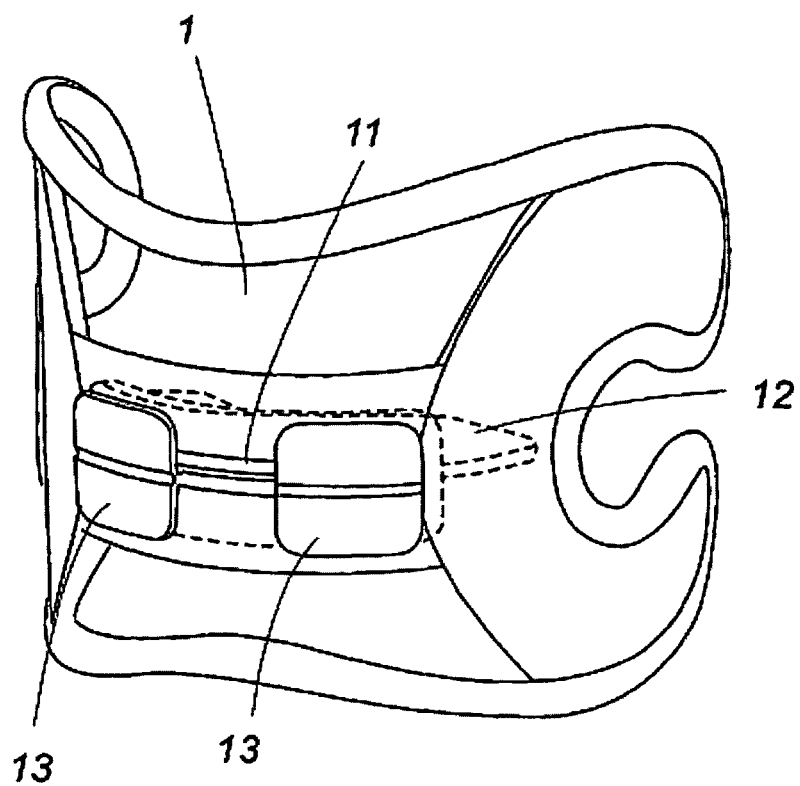
FIG. 9.—Shows a perspective view of the stimulator with the ferrule incorporated.

In FIG. 7 it can be seen how the body (1) that comprises the facial stimulator, in a variant the design, destined to alleviate problems of bruxism, has in its central area a membrane or strip (6) with a horizontal groove (11) apt for receiving additional parts conforming a bite splint, as can be seen in FIGS. 8 and 9, comprising a body (12), made of suitable material, such as resin or plastic, the body (12) having the means to fit to this horizontal groove (11) onto the body (1) of the stimulator.

This body (12) has two parts, a flat back (12a) and an approximately circular sector base, making it apt for placing between the teeth of the lower and upper jaws for biting, conforming the ferrule proper, and another front (2b), perpendicular to the aforementioned parts (2a), which has an approximately rectangular shape, attached by its centre to the edge of the back (2a), and from which emerge frontal and perpendicularly T-section fins (13) which enable it to fit to the body (1) of the stimulator, as these fins (13) are especially designed to be inserted into the horizontal groove (11) made for this purpose on the body of the stimulator (1), as can be seen in FIG. 3. To facilitate the insertion of the fins (13) of the body (12) through the groove (11) of the stimulator, it has a transversal slit at the front (13a) enabling it to be folded.

In this manner, thanks to the elasticity of the materials that both the body (1) of the stimulator and the body (12) of the ferrule are made of, its attachment and detachment can be carried out in a rapid and simple manner, enabling the user or patient to use both elements independently or together.

Figure 10:
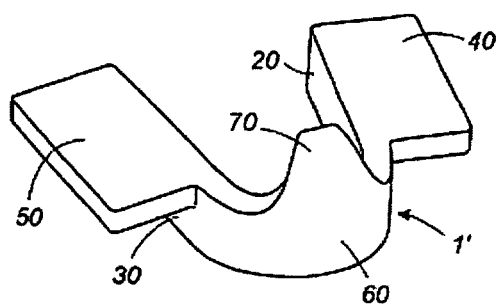
FIG. 10.—Shows a frontal perspective view of an example of the variant of the stimulating element described in the invention, as a mouth stimulating element for the muscles of mastication, in which the general configuration of the particular structure can be seen.
Figure 11:
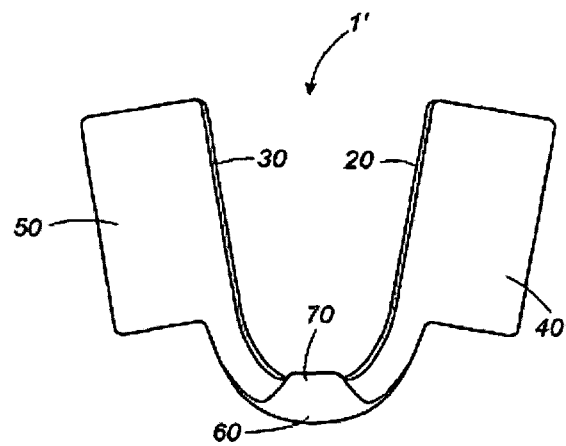
FIG. 11.—Shows a plan view of the example of the stimulating element shown in FIG. 10, displaying its V-shaped configuration.
Figure 12:
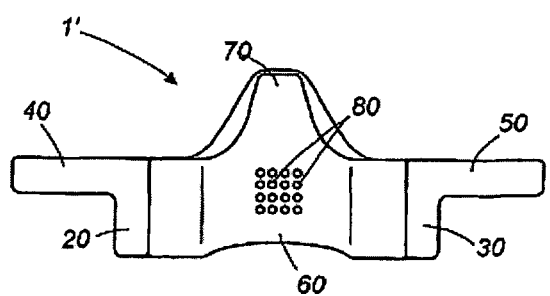
FIG. 12.—Shows a rear elevation view of the invention displayed in FIGS. 10 and 11, where the elevation of the vertex as well as the internal rough areas can be seen.

Finally, with reference to FIGS. 10 to 12, another alternative variant of the invention can be seen, in which the stimulator is configured as an element stimulating the muscles of mastication, comprising a body (1'), also made of biocompatible materials, of sufficient elasticity and softness, which will adopt an approximately V-shaped plan, whose arms are formed by vertical walls (20) and (30) of regular thickness and dimensions suitable for fitting in the interior space of the lower jaw, the upper parts of these walls (20) and (30) having their respective projections (40) and (50) that arise perpendicularly to the exterior, which are designed to become the horizontal biting planes, i.e., apt for horizontal placement between the molar teeth of both lower and upper jaws, respectively on the left and right side of the mouth, to be bitten.

The rounded vertex (60) of the mentioned V, conforming the body of the part (1'), is slightly raised, extended in its centre to determine a central appendix (70) that is slightly curved, forming a sort of frontal shield, apt and destined to support the tongue, with the internal part (1') of this vertex bearing a series of rough spots designed to stimulate the position of the tongue making it tend to be placed on them.

On the inside of this vertex (60) from which the vertical side walls (20) and (30) arise, a series of rough spots have been designed (80) to stimulate the position of the tongue, making it rest on them.

Having described the nature of the present invention in sufficient detail, as well it practical application, no further explanation is considered necessary for any expert in the field to understand its scope and benefits, noting that, within its essential nature, it may be practically used in other embodiments different from those given as examples, and which will also offer the protection referred to here, as long as its fundamental principle is unchanged or unmodified.

The invention claimed is:

1. A face and mouth muscle stimulator configured to stimulate facial muscles, alleviate bruxism and stimulate muscles of mastication comprising:

a body comprised of biocompatible elastic material having an essentially flat approximately oval perimetral shape, the body including opposing side portions and opposing upper and lower zones, the opposing side portions extending at an angle from the respective upper and lower zones, each of the opposing upper and lower zones including a v-shaped recess centrally formed therein, wherein a contoured central opening is defined by the opposing side portions and the opposing upper and lower zones, including the v-shaped recess centrally formed therein, such that the body is open in its center; wherein the opposing side portions have a thickness greater than a thickness of the opposing upper and lower zones, and the body is adapted to be placed between a front side of teeth of a patient and an internal side of lips of the patient such that the opposing side portions stimulate areas of a patient's facial muscles; and stimulation points, each stimulation point comprising a removable protuberance positioned on and projecting outward from a front face of at least one of the opposing upper and lower zones, wherein the stimulation points are configured to act on muscle groups in the mouth of a patient, and wherein the front face of the at least one of the opposing upper and lower zones faces a front of a patient's mouth when the face and mouth muscle stimulator is within the mouth of a patient.

* * * * *